United States Patent [19]

Prencipe et al.

[11] Patent Number: 5,000,944
[45] Date of Patent: Mar. 19, 1991

[54] ZINC-CONTAINING ORAL PRODUCTS WITH REDUCED ASTRINGENCY

[75] Inventors: Michael Prencipe, East Windsor; Shamsul K. Bakar, New Brunswick, both of N.J.

[73] Assignee: Colgate-Palmolive Company, New York, N.Y.

[21] Appl. No.: 364,406

[22] Filed: Jun. 9, 1989

[51] Int. Cl.$^5$ .................. A61K 7/16; A61K 33/30
[52] U.S. Cl. ........................... 424/57; 424/642; 424/643
[58] Field of Search ................. 424/57, 642, 643

[56] References Cited

U.S. PATENT DOCUMENTS

| | | | |
|---|---|---|---|
| 2,191,199 | 2/1940 | Hall | 424/57 |
| 2,216,816 | 10/1940 | Kuever | 424/57 |
| 2,216,821 | 10/1940 | Long | 424/57 |
| 3,095,356 | 6/1963 | Moss | 424/57 |
| 3,475,533 | 10/1969 | Mayrand | 424/57 |
| 3,622,662 | 11/1971 | Roberts et al. | 424/57 |
| 3,699,220 | 10/1972 | Westrate et al. | 424/57 |
| 3,927,202 | 12/1975 | Harvey et al. | 424/57 |
| 3,956,478 | 5/1976 | King et al. | 424/57 |
| 4,080,440 | 3/1978 | DiGiulio et al. | 424/57 |
| 4,083,955 | 4/1978 | Grabenstetter et al. | 424/57 |
| 4,108,980 | 8/1978 | Duff | 424/57 |
| 4,132,773 | 1/1979 | Best et al. | 424/57 |
| 4,139,599 | 2/1979 | Tomlinson et al. | 424/57 |
| 4,152,419 | 5/1979 | Penzak | 424/57 |
| 4,170,634 | 10/1979 | Cordon et al. | 424/57 |
| 4,309,409 | 1/1982 | Coll-Palagus et al. | 424/57 |
| 4,460,565 | 7/1984 | Westrate et al. | 424/57 |
| 4,806,342 | 2/1989 | Gaffar et al. | 424/57 |
| 4,808,400 | 2/1989 | Gaffar et al. | 424/57 |
| 4,808,401 | 2/1989 | Gaffar et al. | 424/57 |
| 4,853,213 | 8/1989 | Thame | 424/58 |
| 4,869,898 | 9/1989 | Gaffar et al. | 424/57 |

FOREIGN PATENT DOCUMENTS 0295116 12/1988 European Pat. Off.

OTHER PUBLICATIONS

Ingram, C.A. 110:198970x (1989), of EP 295116, Dec. 14, 1988.

*Primary Examiner*—Shep K. Rose
*Attorney, Agent, or Firm*—Robert L. Stone; Murray M. Grill

[57] ABSTRACT

A zinc-containing antitartar oral product substantially free of astringency, containing as the essential agent, a zinc/polyphosphate complex having at least about a 50% water solubility, formed by the reaction or interaction of a zinc compound with a potassium or sodium polyphosphate by dissolving a zinc salt in a polyphosphate solution such as pyrophosphate, tripolyphosphate, hexametaphosphate and combinations thereof.

9 Claims, 1 Drawing Sheet

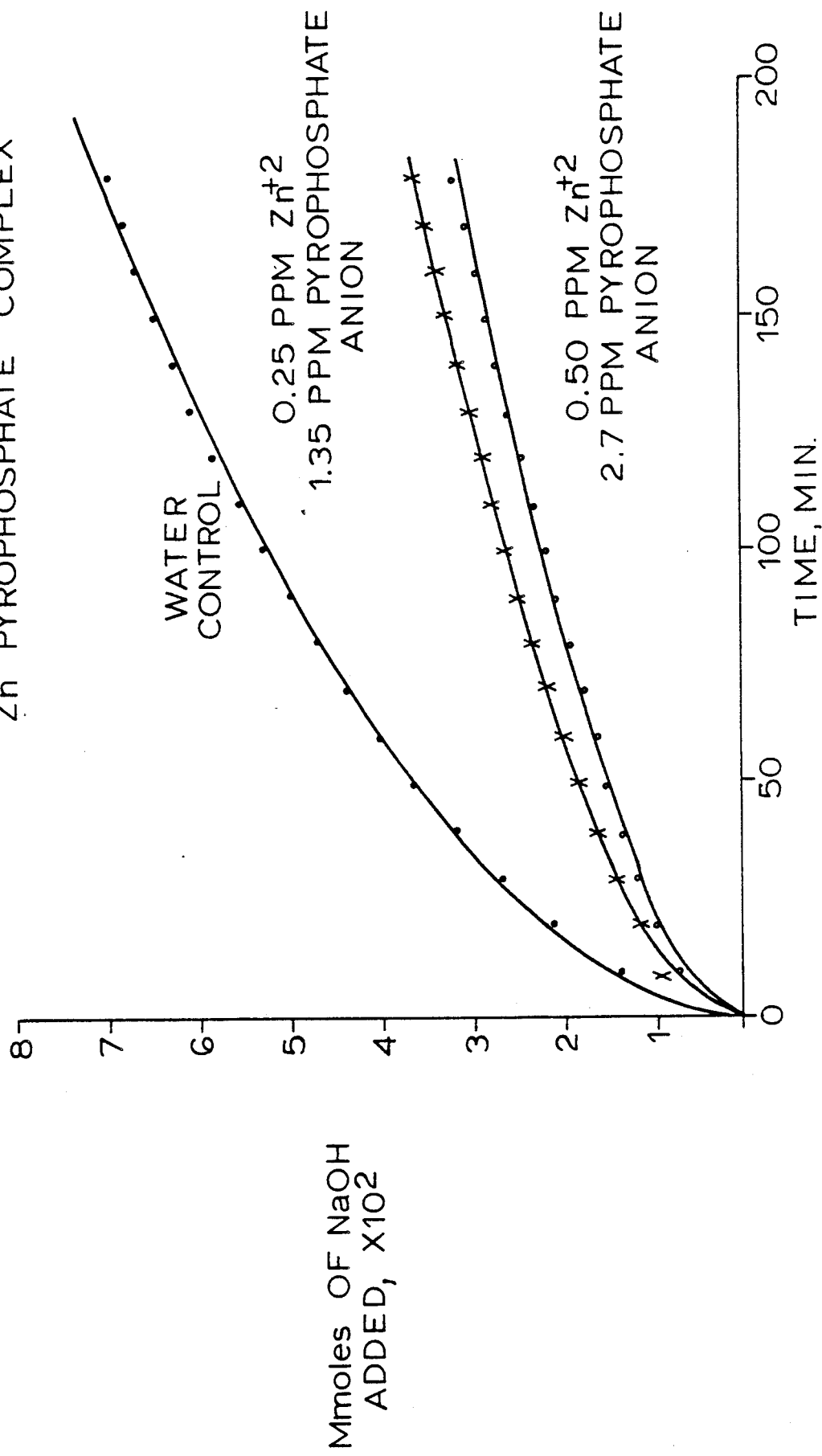

ZINC-CONTAINING ORAL PRODUCTS WITH REDUCED ASTRINGENCY

The present invention relates to novel low astringent oral care products including mouthwashes, dentifrices, lozenges and the like, comprising a combination of zinc salts and polyphosphates.

BACKGROUND OF THE INVENTION

The incorporation of zinc salts into oral dental care products to provide beneficial effects such as antiplaque, anticalculus (that is, antitartar), and deodorant properties is well known in the prior art, as disclosed in U.S. Pat. Nos. 4,138,477, 4,416,867, 4,425,325 and 4,568,540. However, the extreme astringency of water soluble zinc salts such as zinc chloride is a major drawback in its use in oral dental care products. In addition to the unpleasant astringent taste in the mouth, the efficacy against plaque, calculus and odor inhibition is short-lived. Usually the complex formation of zinc with anionic liquids such as citrate reduces its astringency but also reduces its solubility.

Accordingly, sparingly soluble zinc salts such as zinc citrate, zinc $C_{14}$-alkyl maleate, zinc benzoate, zinc caproate, zinc carbonate, etc. have been used in dentifrice formulations to prolong the anti-calculus and antiplaque effectiveness of the zinc ions due to the slow dissolution of the zinc salts in the saliva. The sparingly soluble characteristic of these zinc salts promotes longevity of action against plaque and calculus at the expense of initial or immediate efficacy.

U.S. Pat. Nos. 4,425,325 and 4,416,867 have solved the astringency problem associated with zinc compounds in oral compositions, by adding glycine and adjusting the pH within the range of 4.5 and 9.4 in order to maintain the zinc in solution which is less astringent than a pH below 4.5.

U.S. Pat. No. 4,138,477 also discloses a non-astringet oral composition containing a zinc-polymer complex having a pH of 4.5 to 6, formed by the chelation or reaction of a zinc compound with an anionic polymer containing carboxylic, sulfonic and/or phosphonic acid radicals.

U.S. Pat. No. 4,568,540 discloses oral compositions effective in controlling mouth odor, calculus, plaque and caries, containing active zinc ions and fluoride ions, said zinc ions being provided by zinc salts selected from the group consisting of zinc chloride, zinc sulfate and zinc thiocyanate, and a specific buffering agent to maintain a pH of 3.5 to 6.0 in order to permit the fluoride ions and zinc ions to remain in solution and not precipitate out.

U.S. Pat. No. 4,100,269 discloses an anticalculus dentifrice containing a substantially insoluble zinc compound having a solubility not exceeding about 0.5 to 1% by weight (based on the amount of dissolved zinc ion) at 20° C., in order to avoid astringency. The abrasive with said anticalculus dentifrice compositions must not interact with the zinc compound. Therefore, the commonly used phosphate abrasives or polishing agents cannot be used.

In U.S. Pat. No. 4,627,977 an anticalculus oral composition is disclosed containing a water soluble alkali metal polyphosphate salt, a fluoride ion source, and a water soluble alkali metal or ammonium anionic linear polymeric polycarboxylate salt having a molecular weight of 1,000 to 1,000,000.

None of the above cited prior art discloses low astringent oral care products including mouthwash, dentifrice, lozenge, etc., containing a complex of zinc and a polyphosphate which is unusually effective in reducing the astringency of the zinc and simultaneously provide anti-plaque, anti-tartar and anti-odor efficacy.

SUMMARY OF THE INVENTION

It has been unexpectedly found that the astringency of the zinc salts such as zinc chloride, zinc sulfate, zinc acetate, and the like can be drastically reduced by dissolving said zinc salt in an aqueous polyphosphate solution such as sodium or potassium pyrophosphate, tripolyphosphate, hexametaphosphate, and mixtures thereof, to form a zinc complex which is at least about 50% water soluble. It has also been found that the zinc-/pyrophosphate complex, zinc/tripolyphosphate complex, and zinc/hexametaphosphate complex provide synergistic antitartar activity over the individual components $Zn^{+2}$ and $P_2O_7^{-4}$ (pyrophosphate) etc. ions, and exhibit high antinucleating activity in a seeded crystal growth experiment of hydroxyapatite. Oral formulations including mouthrinse, dentifrice, etc., containing aforesaid zinc/polyphosphate complex, having a range of polyphosphate ion to zinc ion in a molar ratio from about 1:1 to about 5:1, preferably 2:1 to 5:1 have been formulated and found to be substantially completely free of astringency.

Accordingly, a primary object of this invention is to provide an oral product containing a zinc compound having low astringency and antitartar and deodorant properties.

Another object of this invention is to provide a substantially non-astringent antitartar alkaline oral product, containing a zinc/polyphosphate complex which is at least 50% water soluble, in a molar ratio of at least about 1:1 and up to about 5:1 polyphosphate ion:zinc ion in an oral vehicle having a pH of about 6.0 to 9.5.

Still another object of this invention is to provide a zinc-containing oral product substantially free of astringency containing a zinc/polyphosphate complex having synergistically greater antitartar activity than the activity of the individual components of said complex, i.e., zinc ions and polyphosphate ions, in the form of mouthrinses, dentifrices, lozenges, etc.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel substantially non-astringent oral product of this invention has enhanced anti-tartar properties and contains as the essential agent a zinc/polyphosphate complex which is at least about 50% water soluble, in a molar ratio of at least about 1:1 polyphosphate ion:zinc ion and up to about 5:1, in an oral vehicle having a pH of about 6.0 to 9.5.

More specifically, the substantially non-astrigent, stable antitartar oral composition contains as the essential agent a zinc/polyphosphate complex in a molar ratio of at least about 1:1 and preferably 2:1 and up to about 5:1 polyphosphate ion:zinc ion, formed by dissolving a zinc salt in a sodium or potassium polyphosphate aqueous solution, wherein said polyphosphate is selected from the group consisting of pyrophosphate, tripolyphosphate, hexametaphosphate and combinations thereof, and is ionically bound to a physiologically acceptable zinc salt, in an oral vehicle having a pH of about 6.0 to 9.5.

The oral compositions may be in the form of a mouthwash, a dentifrice, a lozenge and the like.

DETAILED DESCRIPTION OF THE INVENTION

It has been unexpectedly found that when a zinc salt such as a chloride, sulfate, acetate, etc., is dissolved in an aqueous polyphosphate solution such as a sodium or potassium pyrophosphate, tripolyphosphate, hexametaphosphate, and combinations thereof, it forms a zinc-polyphosphate complex which is at least 50% water soluble and up to 100% water soluble, so that the astringency of the zinc is drastically reduced.

In its complexes, zinc usually has a coordination number of four, and we are postulating the zinc complex with the pyrophosphate anion to be of the following nature:

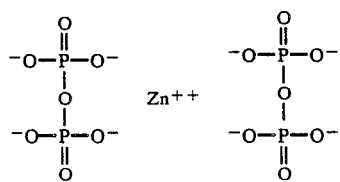

The zinc chloride easily dissolves in a sodium or potassium polyphosphate solution such as a tripolyphosphate and exhibits much lower astringency than a zinc chloride system at the same concentration in the absence of a polyphosphate. This is indicative of the formation of a zinc/polyphosphate complex which reduces the astringency of the zinc. This effect is not limited to tripolyphosphate. The polyphosphates include any linear polyphosphate having from 2 phosphorous atoms (diphosphate) to 21 phosphorous atoms (hexametaphosphate) or more.

It has also been found that a specific $P_2O_7^{-4}/Zn^{+2}$ molar ratio of at least about 2:1 forms a 100% water soluble complex, which is required to prevent immediate precipitation of $Zn_2P_2O_7$ salt in a mouthrinse system, as indicated in Table I. The ratio of polyphosphate to zinc may be increased to about 5:1. The zinc to polyphosphate ratio is preferably 1:2 so that no precipitate is formed in a mouthrinse. However, the low astringency and antiplaque properties of 1:1 zinc/polyphosphate complex having at least about 50% water solubility is retained. The mouthrinse can be used by shaking the mouthrinse prior to use.

Likewise, the tetrasodium pyrophosphate (TSPP) formulations in formulas 2 and 3 were not stable (stable meaning no precipitate formed) at temperatures other than ambient, and this was attributed to the poor solubility of $Na_4P_2O_7$ (5% solubility in water) as shown in Table I.

TABLE I

Stability of Tetrasodium Pyrophosphate (TSPP) Zinc Chloride Tartar Control Rinse Formulas

| Formula | pH | $P_2O_7/Zn$ molar ratio | Stability of formula |
|---|---|---|---|
| 1. 0.25% $ZnCl_2$ 0.5% TSSP | 8.4 | 1:1 | Forms precipitate overnight |
| 2. 0.25% $ZnCl_2$ 1.0% TSPP | 8.6 | 2:1 | No ppt visible for 9 weeks at RT |
| 3. 0.25% $ZnCl_2$ 2.00% TSPP | 8.6 | 4:1 | Large crystals form which are suspected to be TSPP (solubility in water = 5%) |

In order to avoid this complication, tetrapotassium pyrophosphate (TKPP), which is more soluble, is preferably used in lieu of the $Na_4P_2O_7$. An all TKPP tartar control rinse formula having a pH of 9.3 (formula 4) exhibits excellent stability at all aging temperatures, 48.9° C., 37.9° C., sunlight, 4.4° C. and −13.3° C. for a period of nine weeks, (TKPP/$ZnCl_2$ molar ratio of 2.5:1), as shown in Table II. Reduction of pH to 8.5, (formula 6) which also contains a methyl vinyl ether/maleic anhydride copolymer, available from GAF Company as Gantrez (anti-nucleating agent), in the formulation resulted in a rinse formula which was generally stable at all temperatures for nine weeks aging. A minimum of three weeks aging is an acceptable oral product. Reduction of pH to about 7 (formula 8) resulted in precipitation, which was not immediate but occurred after several days of aging. This is indicative of the need to maintain the pH of the tartar control formulations at a pH within the range of 7.7 to 9.5 in order to avoid precipitation and optimize stability of the oral compositions. It is noteworthy that the addition of about 0.1–1% by weight of antinucleating chemicals, which can delay precipitation, may increase the pH range of the compositions to a pH of about 6 to 9.5. Suitable anti-nucleating agents also include polyacrylates such as those available from B.F. Goodrich and known under the Trademark of Carbopol.

TABLE II

Stability of Tetrapotassium Pyrophosphate (TKPP)/Zinc Chloride Tartar Control Rinse Formulas

| Formula | pH | $P_2O_7/Zn$ molar ratio | Stability of Formula | Comments |
|---|---|---|---|---|
| 4. 0.25% $ZnCl_2$ 1.5% TKPP | 9.3 | 2.5:1 | No ppt at all temperatures | |
| 5. 0.25% $ZnCl_2$ 2% TKPP | 9.4 | 3.3:1 | No ppt at all temperatures | 0.10% soluble Zinc ($Zn^+$) 0.96% Pyro ($P_2O_7^-$) |
| 6. 0.25% $ZnCl_2$ 1.50 TKPP | 8.5[1] | 2.5:1 | Formed small amt of ppt after 9 wks at 120° and 40° F. | Formula contains Gantrez[2] |
| 7. 0.25% $ZnCl_2$ 1.5% TKPP | 7.7[3] | 2.5:1 | No ppt forms up to 3 weeks aging | |
| 8. 0.25% $ZnCl_2$ 1.5% TKPP | 7.0 | 2.5:1 | Formed ppt at all temperatures | Formula contains Gantrez[2] |

[1] Adjusted to pH 8.5 by adding 2.5 gm. NaOH (50%).
[2] Copolymer of vinyl methyl ether and maleic anhydride (M.W. 250,000)
[3] pH adjusted to 7.7 by adding 0.9 gm glacial acetic acid.

Analysis of Zn and pyrophosphate ions, conducted for formula 5 containing 0.25% $ZnCl_2$ and 2% TKPP, after 9 weeks aging shows complete recovery of both ions as shown in Table II.

The zinc compound constitutes about 0.25–2.5% by weight of the oral composition. The polyphosphate compound is dependent on the amount of the zinc salt, which must be at least the amount necessary to react with at least 50% of the zinc content to provide a 50% water soluble zinc/polyphosphate complex (a 1:1 molar ratio). Preferably, the amount of polyphosphate necessary to react with the total zinc salt content prevents precipitation of said zinc salt, and provides a completely (100%) water soluble complex (2:1 molar ratio). However, an excess amount of water soluble polyphosphate salt may be present in the composition without resulting in precipitation.

The in vitro antinucleating activity of Zn/Pyrophosphate complex at two different concentrations is compared in FIG. 1 with a water control in a seeded crystal growth experiment of Hydroxyapatite (A. Gaffar and E. C. Moreno, J. Dental Research, 64 (1), 6 (1985). The antinucleating activity of the complex is very high, even at low concentrations (0.25 ppm $Zn^{+2}$, 1.35 ppm Pyrophosphate anion). Even though astringency of zinc is dramatically reduced, its antinucleating activity does not seem to be adversely affected and may even be higher.

FIG. 1 shows that both concentrations of the zinc/pyrophosphate complex solutions inhibit the in vitro formation of hydroxyapatite (HA), as evidenced by the lesser amounts of base (NaOH) consumption recorded over a period of 200 minutes, in comparison to a water control. The antinucleating activity with hydroxyapatite, of a zinc/pyrophosphate complex solution containing 0.5 ppm $Zinc^{+2}$ ions and 2.7 ppm $P_2O_7^{-4}$ (Pyro) ions is very effective in preventing nucleation of hydroxyapatite.

Aqueous solutions of zinc polyphosphate complex may be produced by dissolving a potassium polyphosphate in distilled water, adding a zinc salt in dry form to the polyphosphate solution and completely dissolving the zinc salt, adding water to bring the volume to 1000 cc. The ratio of the number of moles of the phosphate ion to the zinc ion that yields complete solubility of the two powders is at least about 2:1. Below this ratio, all the zinc is not complexed and precipitation occurs. For example, a suitable water soluble zinc/polyphosphate complex is formed by first dissolving 5.1495 grams $K_4P_2O_7$ in 300 cc distilled water, adding 1.0514 grams $ZnCl_2$ to the aqueous $K_4P_2O_7$ solution and dissolving all the zinc chloride, and bringing the volume of water to 1000 cc. The ratio of the number of moles of $P_2O_7^{-4}$ to $Zn^{++}$ that yielded complete solubility of the two powders was 2:1. This solution was calculated to have 504.2 ppm $Zn^{+2}$ ions, and 2,700 ppm pyro ions. The evaluation of its antinucleating activity with hydroxyapatite showed that the $Zn^{+2}$ at 0.5 ppm, and the Pyro ion at 2.7 ppm of the Zn/pyro complex in the above solution, was very effective in preventing nucleation of hydroxyapatite.

The aqueous solution of the zinc/polyphosphate complex may be incorporated into oral compositions generally, such as mouthrinses, dentifrices, lozenges and the like, containing a dental vehicle. Likewise, the at least 50% water soluble complex may be formed in situ, during the preparation of said oral compositions.

While particularly good results in terms of tartar control and other salutary effects in the oral cavity and on tooth surfaces, have thus far been obtained by applying simply the aqueous solutions of the zinc/polyphosphate complex, it will be understood that it is within the broader aspect of the invention to incorporate said complex into oral compositions generally, such as clear or cloudy mouth rinses and transparent or opaque toothpastes, troches, chewing gum, tablet or powder containing a dental vehicle. Likewise, the complex may be formed in situ, during the preparation of said oral compositions.

The vehicle, often referred to as a dental vehicle contains liquids and solids in a dentifrice. In general, the liquid comprises water and/or a humectant such as glycerine, sorbitol, propylene glycol or polyethylene glycol 400 or 600 including suitable mixtures thereof. It is usually advantageous to use a mixture of both water and one or two humectants. The total liquid content is generally about 20–90 percent by weight of the vehicle. In transparent and translucent vehicles, the liquid content of the toothpaste may be about 20–90 percent by weight, while in opaque vehicles the total liquid content is usually about 20–50 percent by weight. The preferred humectants are glycerine, sorbitol, and polyethylene glycol.

The solid portion of the vehicle is a gelling agent. In the instant invention the gelling agent includes alkali metal carboxymethyl cellulose, hydroxyethyl cellulose, hydroxymethyl cellulose in an amount of at least about 0.5 percent by weight of the vehicle. Additional gelling agents may also be present. Gelling agents which may be additionally present include viscarin, gelatin, starch, glucose, sucrose, polyvinyl pyrollidone, polyvinyl alcohol, gum tragacanth, gum karaya, hydroxypropyl cellulose, methyl cellulose, carboxyethyl cellulose, sodium alginate. Laponite CP or SP, which are each synthetic inorganic complex silicate clays sold under trademark by Laporte Industries, Ltd., and magnesium aluminum silicate gel. The solid portion or gelling agent of the vehicle is typically present in an amount of about 0.5–5 percent by weight of the toothpaste and preferably about 0.5–2 percent by weight.

Any suitable substantially water-insoluble polishing agent may be added to the gel vehicle of the dentifrice. There is a relatively large number of such materials known in the art. Representative materials include, for example, dicalcium phosphate, tricalcium phosphate, aluminum hydroxide, magnesium carbonate, calcium carbonate, calcium pyrophosphate, calcium sulfate, bentonite, alumina, hydrated alumina, aluminum silicate, zirconium silicates, silica, including suitable mixtures thereof. In general, these polishing agents will comprise a major proportion by weight of the solid ingredients. The polishing agent content is variable, but will generally be up to about 75 percent by weight of the total composition, generally about 20–75 percent; although, as indicated below, even lower amounts of polishing agent can be employed.

Any suitable surface-active or detersive material may be incorporated in the gel vheicle. Such compatible materials are desirable to provid additional detersive, foaming and antibacterial properties depending upon the specific type of surface-active material and are selected similarly. These detergents are water-soluble organic compounds usually, and may be anionic, nonionic, or cationic in structure. It is preferred to use the water-soluble non-soap or synthetic organic detergents, usually. Suitable detersive materials are known and include, for example, the water-soluble salts of higher fatty acid monoglyceride monosulfate detergent (e.c., sodium coconut fatty acid monoglyceride monosulfate), higher alkyl sulfates (e.g., sodium lauryl sulfate), alkyl aryl sulfonate (e.g., sodium dodecyl benzene sulfonate), higher fatty acid esters of 1,2-dihydroxypropane sulfonate) and the like.

The various surface-active materials may be used in any suitable amount, generally from about 0.05 to about 10 percent by weight, and preferably from about 0.5 to 5 percent by weight of the dentifrice composition.

The dentifrice of this invention may also contain conventional ingredients such as coloring or whitening agents, preservatives, flavoring or sweetening materials, antimicrobial agents such as chlorhexidine, antiplaque agents such as zinc-polymer combinations (U.S. Pat. No. 4,138,477), and preferably compounds which provide fluorine-containing ions such as sodium fluoride, stannous fluoride and sodium monofluorophosphate. These additional ingredients may each be added to the dentifrice in minimal amounts of up to 5% by weight, and preferably up to 1%, provided they do not interfere with the antitartar, anti-astringency and stability properties of the finished product.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol, water and, often, humectant.

Such oral preparations are typically applied by brushing the teeth with a dentifrice or toothpaste or rinsing the oral cavity with a mouthrinse for 30–90 seconds or in the case of a lozenge, candy or gum by sucking or chewing in the oral cavity or in the case of a mouthspray by spraying into contact with oral surfaces at least once daily. Typical oral preparations of the invention which can be applied in this manner are set forth in the

| Example 1 Mouthrinse | | |
|---|---|---|
| Ingredients | | Percent |
| Ethanol (95%) | | 10.00 |
| Flavor | | 0.25 |
| Polyethylene Glycol (PEG) - 400 | | 2.00 |
| Glycerine | | 10.00 |
| TSPP (Tetra Sodium pyrophosphate) | | 0.50 |
| ZnCl$_2$ | | 0.25 |
| Sodium Saccharin | | 0.03 |
| FD&C Blue #1 (1% Soln) | | 0.05 |
| Deionized Water (DI) | Q.s. | 100.00 | pH = 8.4

The mouthrinse is prepared by forming two separate solutions, an ethanol solution containing the flavor, polyethylene glycol and glycerine, and an aqueous solution containing the zinc/polyphosphate complex and sweetener; combining the two solutions with mixing and adding the color to complete the mouthwash.

More specifically, the flavor is added to the ethanol with light mixing, followed by the addition of polyethylene glycol, and mixing with a magnetic stirrer for about five minutes, followed by the addition of glycerin and mixing until well dispersed into the ethanol solution.

In a separate container, the tetra sodium pyrophosphate is dissolved in the deionized water by mixing with a magnetic stirrer until completely dissolved, adding zinc chloride and mixing until completely dissolved in the aqueous solution, adding saccharin and mixing about two minutes.

Lastly adding the two solutions and mixing about one minute, followed by the addition of the color, to complete the mouthwash.

Although this mouthrinse is unstable, forms a precipitate because of a 1:1 molar ratio of the pyrophosphate ion to zinc ion, it is an oral product having reduced astringency and effective antitartar activity.

| Example 2 Mouthrinse | | |
|---|---|---|
| Ingredients | | Percent |
| Ethanol (95%) | | 10.00 |
| Flavor | | 0.25 |
| PEG-400 (Polyethylene Glycol) | | 2.00 |
| Glycerine | | 10.00 |
| TSPP (Tetrasod. pyrophosphate) | | 1.00 |
| ZnCl$_2$ | | 0.25 |
| Sod. Saccharin | | 0.03 |
| FD&C Blue #1 (1% Soln) | | 0.05 |
| Water, DI | Q.s. | 100.00 | pH = 8.6

This mouthrinse is prepared according to the procedure of Example 1.

Aging tests performed on this product for nine weeks at room temperature, 4.4° C. and −13.3° C. show no precipitate; small crystals form on the sidewalls of the container at 48.9° C. and 37.9° C.

| Example 3 Mouthrinse | | |
|---|---|---|
| Ingredients | | Percent |
| Ethanol (95%) | | 10.00 |
| Flavor | | 0.25 |
| PEG-400 | | 2.00 |
| Glycerine | | 8.00 |
| TSPP (Tetrasodium pyrophosphate) | | 2.00 |
| ZnCl$_2$ | | 0.25 |
| Sod. Saccharin | | 0.03 |
| FD&C Blue #1 (1% Soln) | | 0.05 |
| Water, DI | Q.s. | 100.00 | pH = 8.6

This mouthrinse is prepared according to the procedure of Example 1.

This mouthrinse is stable for six weeks of aging at 48.9° C., 37.9° C. and sunlight; the color is slightly faded.

| Example 4 Mouthrinse | | |
|---|---|---|
| Ingredients | | Percent |
| Ethanol (95%) | | 10.00 |
| Flavor | | 0.25 |
| PEG-400 | | 2.00 |
| Glycerine | | 10.00 |
| NaF | | 0.025 |
| TKPP | | 1.50 |
| ZnCl$_2$ | | 0.25 |
| Sod. Saccharin | | 0.03 |
| FD&C Blue #1 (1% Soln) | | 0.05 |
| Water, DI | Q.s. | 100.00 | pH = 9.3

This mouthrinse is prepared according to the procedure of Example 1 except that the NaF is also dissolved in the ethanol solution, and an aqueous solution of TKPP is formed in lieu of the TSPP.

This tartar control, low astringent mouthrinse is stable at room temperature, 48.9° C., 37.9° C., sunlight 4.4° C. and −13.3° C. after aging for nine weeks.

Example 5 Mouthrinse

| Ingredients | Percent |
|---|---|
| Ethanol (95%) | 10.00 |
| Flavor | 0.25 |
| PEG-400 | 2.00 |
| Glycerine | 8.00 |
| TKPP | 2.00 |
| ZnCl$_2$ | 0.25 |
| Sod. Saccharin | 0.03 |
| FD&C Blue #1 (1% Soln) | 0.05 |
| Water, DI Q.s. | 100.00 | pH = 9.4

This mouthrinse is prepared according to the procedure of Example 1.

The mouthrinse exhibits excellent cosmetic stability at all temperatures except that slight color fading occurs in sunlight after six weeks of aging.

Example 6 Mouthrinse

| Ingredients | Percent |
|---|---|
| Ethanol (95%) | 10.00 |
| Flavor | 0.25 |
| PEG-400 | 2.00 |
| Glycerine | 10.00 |
| TKPP | 1.50 |
| ZnCl$_2$ | 0.25 |
| Sod. Saccharin | 0.03 |
| FD&C Blue #1 (1% Soln) | 0.05 |
| NaF | 0.025 |
| Gantrez (15%)[1] | 1.350 |
| Water, DI Q.s. | 100.00 | original pH = 7.0
pH adjusted to 8.5 with about 2.5 gm. NaOH (50%)

This mouthrinse is prepared according to the procedure of Example 1, except that the NaF and the Gantrez polymer is dissolved in the combined solutions, and NaOH is added to adjust the pH of the mouthrinse to 8.5.

This mouthrinse is stable at all temperatures after aging for nine weeks.

Example 7 Mouthrinse

| Ingredients | Percentage |
|---|---|
| Ethanol (95%) | 10.00 |
| Flavor | 0.25 |
| PEG-400 | 2.00 |
| Glycerine | 10.00 |
| NaF | 0.025 |
| TKPP | 1.50 |
| ZnCl$_2$ | 0.25 |
| Sod. Saccharin | 0.03 |
| FD&C Blue #1 (1% Soln) | 0.05 |
| Acetic acid 9% to pH 7.7 | |
| Water, DI Q.s. | 100.00 | pH = 9.6 (as is)
pH adjusted to 7.7 with 0.9 gm glacial acetic acid.

This mouthrinse was prepared according to Example 1, except that glacial acetic acid was added to adjust the pH to 7.7, in order to determine the affect of pH below 8.5.

This composition exhibits stability at 4.4° C. and −13.3° C. for three to six weeks. This composition also showed no precipitate at other temperatures, up to three weeks of aging.

Example 8 Mouthrinse

| Ingredients | Percent |
|---|---|
| Ethanol (95%) | 10.00 |
| Flavor | 0.25 |
| PEG-400 | 2.00 |
| Glycerine | 10.00 |
| TKPP | 1.50 |
| ZnCl$_2$ | 0.25 |
| Sod. Saccharin | 0.03 |
| FD&C Blue #1 (1% Soln) | 0.05 |
| NaF | 0.025 |
| Gantrez (15% Soln) | 1.35 |
| Water, DI Q.s. | 100.00 | pH = 7.0 (as is)

This low pH mouthrinse is prepared according to the procedure of Example 6, except that no NaOH is added to increase the pH 7 of the mouthrinse.

This mouthrinse is not stable and exhibits precipitates at the bottom of the aging containers at all temperatures, but is non-astringent antitartar mouthrinse.

Example 9 Mouthrinse

| Ingredients | Percent |
|---|---|
| A | |
| Ethanol (95%) | 10.00 |
| Flavor | 0.22 |
| PEG-400 | 2.00 |
| Glycerine | 8.00 |
| B | |
| Water, DI | 78.70 |
| STPP (Sodium tripolyphosphate) | 0.75 |
| ZnCl$_2$ | 0.25 |
| Sodium Saccharin | 0.03 |
| FD&C Blue #1 (1% Soln) | 0.05 | pH = 7.0

Shows white ppt. after standing 2 hours. This mouthrinse may be shaken prior to use.

Example 10 Mouthrinse

| Ingredients | Percent |
|---|---|
| Ethanol (95%) | 10.00 |
| Flavor | 0.25 |
| PEG-400 | 2.00 |
| Glycerine | 8.00 |
| STPP | 1.00 |
| ZnCl$_2$ | 0.25 |
| Sodium Saccharin | 0.03 |
| FD&C Blue #1 (1% Soln) | 0.05 |
| Water, DI Q.s. | 100.00 | pH = 7.8

Shows white ppt. after overnight standing due to the absence of an anti-nucleating agent. The molar ratio of polyphosphate to Zn ion is 2:1. This product is a low astringent, antitartar mouthrinse which can be used after shaking the mouthrinse.

Example 11 Mouthrinse

| Ingredients | Percent |
|---|---|
| Ethanol (95%) | 10.00 |
| Flavor | 0.25 |

Example 11
Mouthrinse

| Ingredients | | Percent |
| --- | --- | --- |
| PEG-400 | | 2.00 |
| Glycerine | | 8.00 |
| STPP | | 2.00 |
| ZnCl$_2$ | | 0.25 |
| Sodium Saccharin | | 0.03 |
| FD&C Blue #1 (1% Soln) | | 0.05 |
| Water, DI | Q.s. | 100.00 | pH = 9.5

This product exhibits stability over a period of aging for nine weeks at 48.9° C.

Example 12
Dentifrice
Toothpaste

| Ingredients | Percent |
| --- | --- |
| Water, DI | 30.00 |
| ZnCl$_2$ | 1.25 |
| Polyethylene glycol (MW 600) | 30.60 |
| Hydroxyethyl Cellulose | 0.60 |
| Sodium saccharin | 0.40 |
| NAF | 0.25 |
| NaOH (50% soln.) | 2.00 |
| Gantrez (15% soln.) | 7.00 |
| (TKPP) Tetrapotassium pyrophosphate | 3.80 |
| (TSPP) Tetrasodium pyrophosphate | 1.00 |
| Zeodent 113[1] | 16.00 |
| Sylox-15[2] | 4.00 |
| TiO$_2$ | 0.50 |
| Flavor | 1.10 |
| SLS (Sodium Lauryl Sulfate) | 1.50 | pH = 8.7
% Soluble Zn = 75%
[1]Abrasive silica supplied by J. W. Huber Co.
[2]Thickening silica from W. R. Grace Co.

The dentifrice is prepared by forming an aqueous solution of the zinc/polyphosphate complex, and the remaining ingredients are admixed with agitation to form a base paste, which is then mixed with the aqueous solution containing the zinc/polyphosphate complex; alternatively the zinc/polyphosphate complex may be formed in situ.

More specifically, the dentifrice is prepared by forming a dry mix of sodium saccharin, sodium fluoride, TKPP and TSPP and hydroxyethyl cellulose (gelling agent), adding said dry mix to the polyethylene glycol (humectant) and mixing for about fifteen minutes, adding an aqueous solution of zinc chloride and mixing about two minutes, and lastly adding the remaining ingredients such as water insoluble polishing agents, TiO$_2$, SLS, Gantrez polymer solution, NaOH solution, flavor and the blue colorant, and mixing for about five minutes to complete the dentifrice.

The highest recoverable Zn in the supernatant liquid complex of a 10:1 dentifrice/water slurry containing Zn/polyphosphate complex was found to be 75% of the total Zn in dentifrice formulation Example 12. This measurement was done prior to aging of the dentifrice. The molar ratio of polyphosphate to zinc ion is less than 2:1 in this toothpaste which exhibits precipitation and separation. This example illustrates that a minimum molar ratio of 2:1 phosphate to zinc is required to completely solubilize the zinc/polyphosphate complex.

Example 13
Dentifrice
Toothpaste

| Ingredients | | Percent |
| --- | --- | --- |
| Zinc Chloride | | 1.00 |
| Tetrasodium pyrophosphate (TSPP) | | 4.00 |
| Natrosol 250M[1] | | 0.60 |
| Sodium Saccharin | | 0.40 |
| Sodium Fluoride | | 0.25 |
| Sodium Hydroxide (50%) | | 1.50 |
| Glycerine | | 27.00 |
| Carbowax - 600[2] | | 6.00 |
| FD&C Blue #1 (1.0% Solution) | | 0.40 |
| Zeodent 113[3] | | 18.00 |
| Sylox - 15[4] | | 8.00 |
| Flavor | | 1.00 |
| Sodium lauryl sulfate | | 1.50 |
| Deionized water, | q.s. | 100.00 | pH = alkaline
[1]Hydroxyethyl cellulose
[2]Polyethylene glycol (MW 600)
[3]Abrasive silica supplied J. W. Huber Co.
[4]Thickening silica from W. R. Grace Co.

The dentifrice is prepared according to the procedure of Example 12, except that the glycerine replaces most of the polyethylene glycol humectant, and the amounts of zinc chloride is 1% and the amount of tetrasodium pyrophosphate is 4%, a molar ratio of 2:1, which is within the range required to completely solubilize the zinc polyphosphate complex.

An effective amount, e.g., about 0.25-2.5% zinc compound and 1-5% polyphosphate is also incorporated in an inert carrier or dissolved in a suitable vehicle in the formulation of chewing gums and lozenges. Similarly, the zinc polyphosphate complex is also incorporated into a mouth spray. A typical lozenge formula contains the following ingredients, in percent by weight, based on the weight of the total formulation:

| | |
| --- | --- |
| 75% to 98% | Sugar |
| 1% to 20% | Corn Syrup |
| .1% to 1% | Flavor oil |
| 0% to .03% | Colorant(s) |
| .1% to 5% | Tableting Lubricant |
| .2% to 2% | Water |
| 1% to 5% | Polyphosphate |
| 0.25% to 2.5% | Zn compound |

Sugarless pressed candy may also be formulated to include the complex of this invention. For products of this type, which usually contain powdered sorbitol instead of sugar, synthetic sweeteners are mixed with the powdered sorbitol and flavor(s), colorant(s) and a tablet lubricant are then added. The formula is introduced into a tablet machine to shape the final product. A typical sugarless pressed candy contains the following ingredients, in percent by weight, based on the weight of the total formulation:

| | |
| --- | --- |
| 98% to 99.5% | Sorbitol |
| .1% to .9% | Flavor(s) |
| 0% to .02% | Synthetic Sweeteners |
| 0% to .03% | Colorant(s) |
| .05% to 1% | Tableting Lubricant |

Obviously many variations of the above described procedures may be used to prepare pressed candies.

A typical chewing gum may contain the following ingredients, in percent by weight based on the weight of the total gum formulation:

| Ingredients | Weight Percent |
| --- | --- |
| Gum Base | From about 10% to about 40% |
| Sicrose | From about 50% to about 75% |
| Corn Syrup or Glucose | From about 10% to about 20% |
| Flavor Material | From about 0.4% to about 5% |
| Polyphosphate | From about 1% to about 5% |
| Zn compound | From about 0.25% to about 2.5% |

An alternate chewing gum formulation is as follows:

| Ingredients | Weight Percent |
| --- | --- |
| Gum Base | From about 10% to about 50% |
| Binder | From about 3% to about 10% |
| Filler (Sorbitol, Mannitol or combination thereof) | From about 5% to about 80% |
| Artificial Sweetener and Flavor | From about 0.1% to about 5% |
| Polyphosphate | From about 1% to about 5% |
| Zn Compound | From about 0.25% to about 2.5% |

In certain sugarless gums, there is used as the binder ingredient a solution of sorbitol in water containing from about 10% to about 80%, preferably from about 50% to about 75% by weight of sorbitol in $H_2O$. In others, there is used a gum acacia-in-water system containing from about 30% to about 60%, preferably from about 45% to about 50% by weight of gum acacia powder.

The above chewing gum formulations are exemplary only. Many additional formulations are described in the prior art, and in carrying out this invention, such formulations can be employed. It is also possible to prepare an acceptable chewing gum product containing a gum base, flavoring material and a zinc/polyphosphate complex according to the teaching of this invention.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutyleneisoprene copolymer, paraffin, petroleum wax, polyethylene, polyisobutylene, polyvinylacetate, etc.; plasticizers such as lanolin, stearic acid, sodium stearate, potassium stearate, etc.

Although this invention has been described with reference to specific examples, it will be apparent to one skilled in the art that various modifications may be made thereto which fall within its scope.

We claim:

1. An anti-tartar oral composition comprising as the anti-tartar agent, an anti-tartar effective amount of a zinc/polyphosphate complex which is at least about 50% water-soluble, wherein said polyphosphate ion is a linear polyphosphate ion having from 2 to 21 phosphorous atoms and wherein the molar ratio of said polyphosphate ion to said zinc ion ranges from about 1.1 to about 5.1; said complex being present in an oral vehicle having a pH of about 6.0 to about 9.5.

2. The composition of claim 1 wherein said polyphosphate ion is selected from the group consisting of pyrophosphate, tripolyphosphate, hexametaphosphate and combinations thereof.

3. The composition in accordance with claim 1 wherein the zinc ion is present in the composition in a quantity equivalent to about 0.25–2.5% by weight of zinc chloride based on the weight of said composition.

4. The composition of claim 1 wherein the molar ratio of said polyphosphate ion to said zinc ion ranges from about 2.2:1 to 5:1.

5. The composition of claim 1 wherein said zinc/phosphate complex is the reaction product of zinc chloride and tetrasodium pyrophosphate.

6. The composition of claim 4 wherein said zinc polyphosphate complex is the reaction product of zinc chloride and tetrapotassium pyrophosphate.

7. The composition of claim 1 wherein said zinc polyphosphate complex is the reaction product of zinc chloride with a mixture of tetrapotassium pyrophosphate and tetrasodium pyrophosphate.

8. An anti-tartar mouthrinse comprising as the anti-tartar agent an anti-tartar effective amount of a zinc/polyphosphate complex which is at least about 50% water soluble wherein said polyphosphate ion is reaction product of zinc chloride and tetrapotassium pyrophosphate and said molar ratio of said polyphosphate ion to said zinc ion ranges from about 1:1 to about 5:1; said mouthrinse having a pH of about 6.0 to 9.5.

9. An anti-tartar dentifrice comprising as the anti-tartar agent an anti-tartar effective amount of a zinc polyphosphate complex which is at least about 50% water soluble wherein said zinc/polyphosphate complex is the reaction product of zinc chloride and tetrapotassium pyrophosphate and wherein the molar ratio of said phosphate ion to said zinc ion ranges from about 1:1 to about 5:1; said dentifrice having a pH of about 6.0 to about 9.5.

* * * * *